United States Patent [19]

Farkas

[11] Patent Number: 5,246,423
[45] Date of Patent: Sep. 21, 1993

[54] REMOTE CANNULA REMOVAL HYPODERMIC SYRINGE

[76] Inventor: Paul J. Farkas, 2 Mill St., #306, Princeton, Me. 04668

[21] Appl. No.: 786,893

[22] Filed: Nov. 1, 1991

[51] Int. Cl.$^5$ ............................................ A61M 5/00
[52] U.S. Cl. .................... 604/110; 604/218; 604/240; 128/919
[58] Field of Search ............... 604/110, 186, 187, 207, 604/208, 218, 228, 239, 240, 246, 192, 195, 196, 198, 263, 241; 128/919

[56] References Cited

U.S. PATENT DOCUMENTS

| | | |
|---|---|---|
| Re. 28,713 | 2/1976 | Stevens et al. . |
| 3,234,944 | 2/1966 | Stevens et al. . |
| 3,320,954 | 12/1967 | Cowley . |
| 3,648,695 | 3/1972 | Bowen . |
| 3,712,302 | 1/1973 | Burke et al. . |
| 4,026,287 | 5/1977 | Haller . |
| 4,027,669 | 6/1977 | Johnston et al. . |
| 4,220,151 | 9/1980 | Whitney .............................. 604/110 |
| 4,233,975 | 11/1980 | Yerman . |
| 4,888,002 | 12/1989 | Braginetz et al. .................... 604/195 |
| 4,950,251 | 8/1990 | Haining ................................ 604/195 |
| 4,973,308 | 11/1990 | Borras et al. ........................ 604/110 |
| 4,986,813 | 1/1991 | Blake et al. .......................... 604/110 |
| 4,995,874 | 2/1991 | Strickland ............................ 604/195 |
| 5,000,738 | 3/1991 | LaVallo et al. ...................... 604/110 |
| 5,045,063 | 9/1991 | Spielberg ............................. 604/110 |
| 5,104,378 | 4/1992 | Haber et al. ......................... 604/110 |
| 5,112,316 | 5/1992 | Venturini ............................. 604/195 |

FOREIGN PATENT DOCUMENTS

| | | | |
|---|---|---|---|
| 0276150 | 7/1988 | European Pat. Off. ............. | 604/110 |
| 2601512 | 3/1977 | Fed. Rep. of Germany ...... | 604/110 |
| 2237511 | 5/1991 | United Kingdom ................ | 604/110 |
| 8504590 | 10/1985 | World Int. Prop. O. ........... | 604/218 |
| 9011100 | 10/1990 | World Int. Prop. O. ........... | 604/110 |

Primary Examiner—John D. Yasko
Assistant Examiner—Mark O. Polutta
Attorney, Agent, or Firm—Robert M. Sperry

[57] ABSTRACT

Disclosed is a hypodermic syringe with several embodiments teaching the safe disposal of the cannula and hub of the syringe into a container such as a SHARPS CONTAINER without the need of replacing the needle cover thus eliminating the very real danger of an accidental stick of a finger or hand of the technician with a contaminated needle. The preferred embodiment allows the plunger to stop at a first resistance and when the needle is removed from the subject and placed over the disposal container, continued forward motion forces the hub and needle to separate from the barrel thus involving the use of only one hand and eliminating the need to bring the others hand anywhere near the contaminated needle.

9 Claims, 4 Drawing Sheets

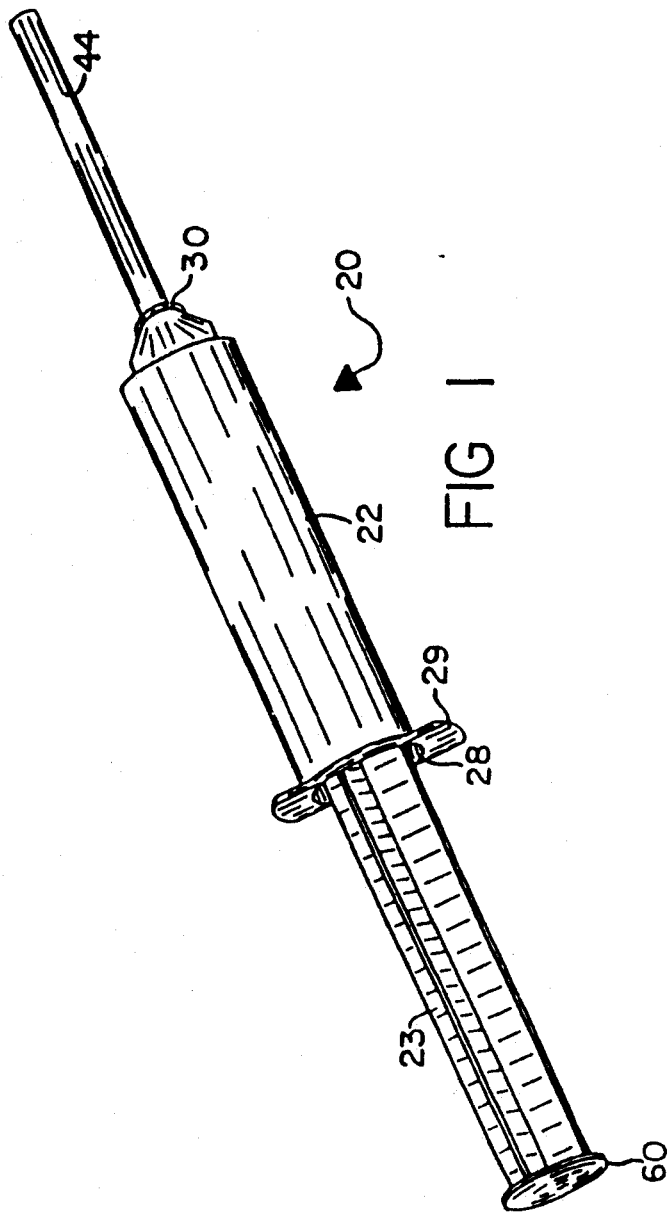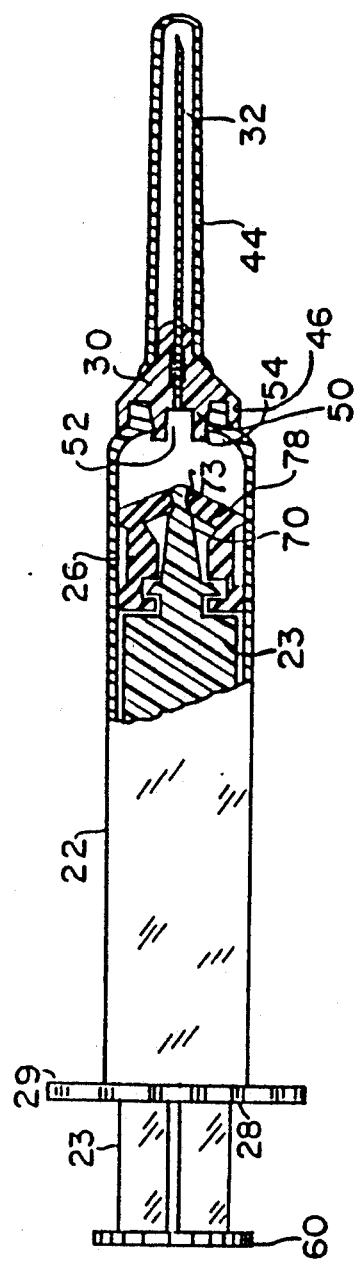

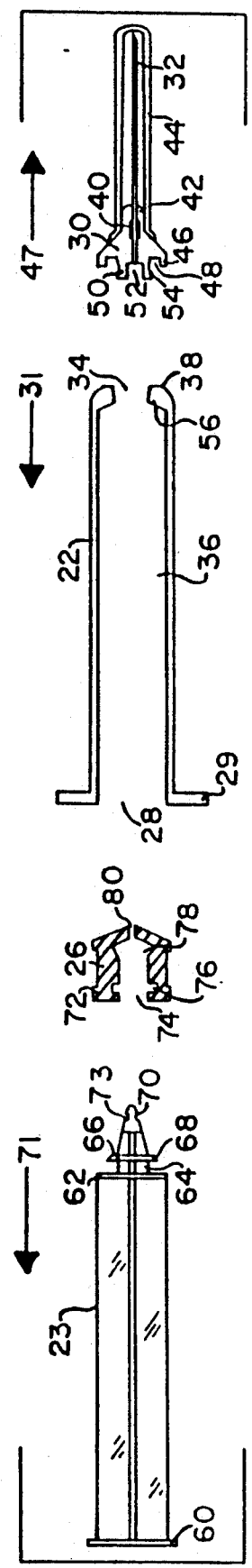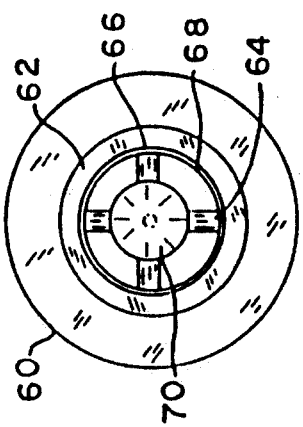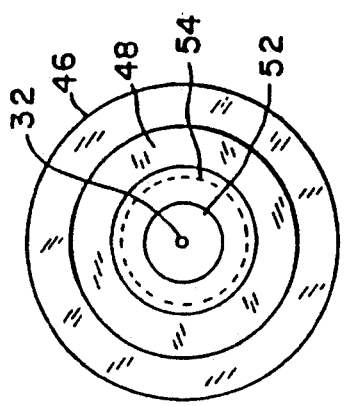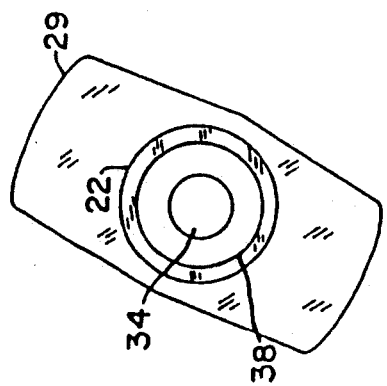

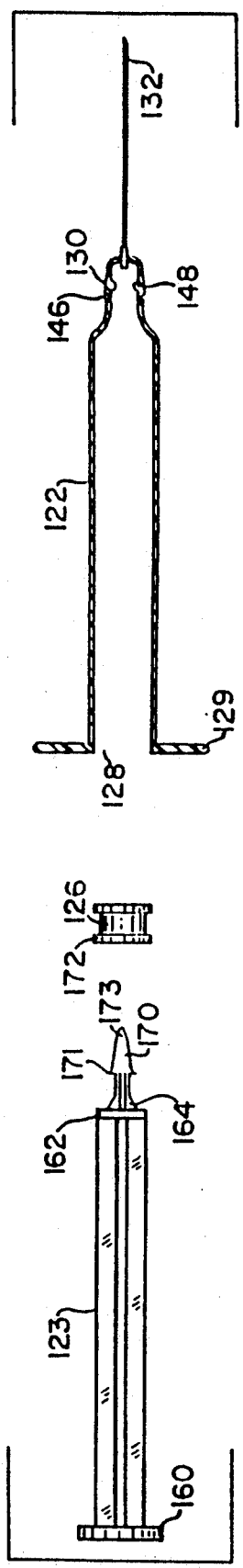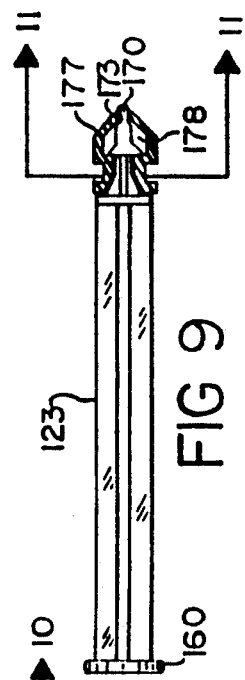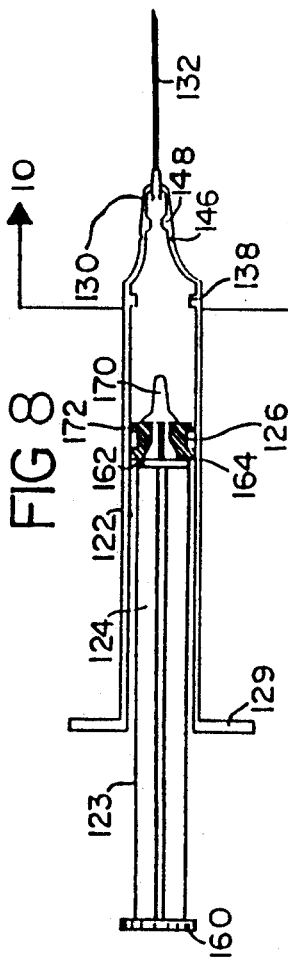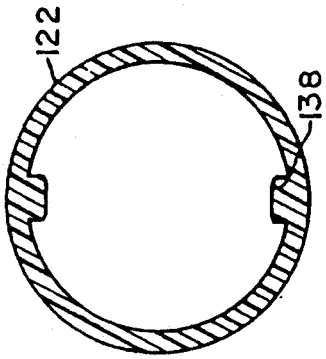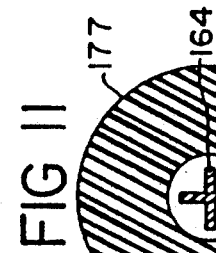

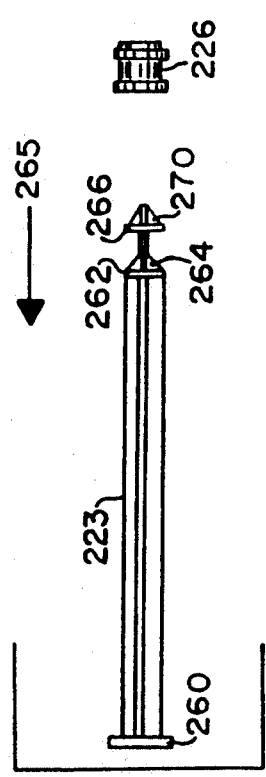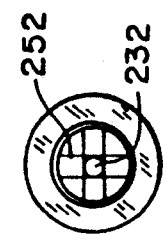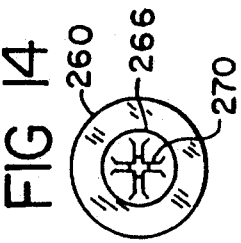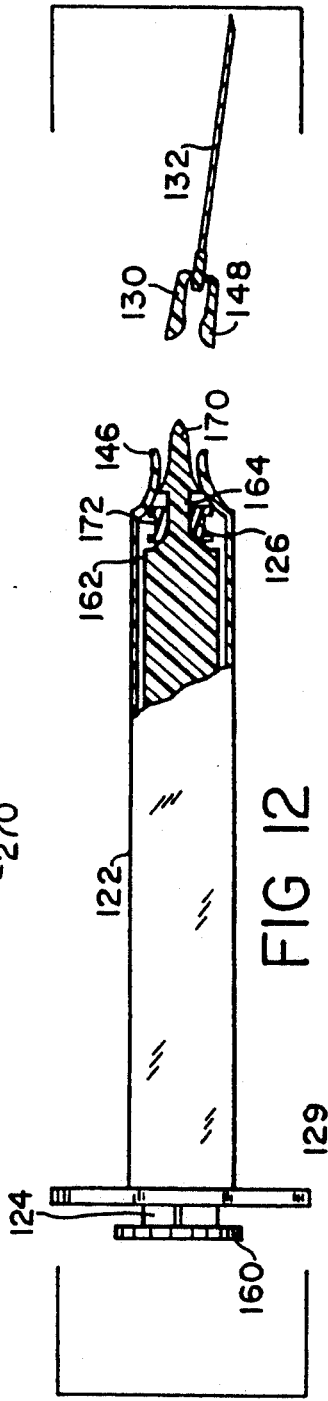

REMOTE CANNULA REMOVAL HYPODERMIC SYRINGE

FIELD OF THE INVENTION

This invention relates to hypodermic syringes and more particularly to syringes which allow the cannulas to be removed by remote means.

BACKGROUND OF THE INVENTION

For many years the typical hypodermic syringe has posed certain hazards to the community. Physicians, Nurses, and other healthcare professionals are keenly aware of the risks associated with use and disposal of these syringes. These risks include the possibility of physical injury by an inadvertent needle puncture and the more serious threat of cross-contamination and ensuing infection from an advertent "needle-stick" injury. Contracting a serious or deadly infection such as Acquired Immune Deficiency Syndrome (A.I.D.S.) or Hepatitis B from a contaminated hypodermic syringe is a very real possibility for healthcare workers. After penetration of an infected patient the cannula of the hypodermic syringe is contaminated by the blood of the patient. When the syringe is removed from the patient it becomes an immediate source of infection and poses a serious health threat to any individual who may come in contact with it.

Over the years as healthcare workers have become more aware of the dangers associated with the hypodermic syringe a number of strategies evolved to deal with the risks.

Needle covers which fit over the cannulas have been used to prevent needle-stick injuries. The hypodermic syringes are typically equipped with these covers or "caps" when they are shipped from the factory. At the clinical site the healthcare worker removes the cap, aspirates or otherwise inserts a medication into the syringe, and then injects the patient. The syringes may also be used to withdraw bodily fluids such as blood. The cannula is often re-capped by the clinician immediately after use to prevent a subsequent accidental needle puncture. This act in itself is hazardous to the clinician since most needle-stick injuries occur during recapping procedures.

The other most common method of dealing with the contaminated syringe is to dispose of the entire syringe in a thick walled plastic container which can be carefully disposed of later. After the syringe has been used it is placed into the SHARPS CONTAINER in its entirety without recapping the needle. The disadvantage of this method is that the sharps container must typically be a gallon or more in size in order to conveniently accommodate enough syringes to make disposal convenient. This method requires a healthcare facility to maintain and dispose of large numbers of bulky SHARPS CONTAINERS which contain used intact syringes. These syringes then become easy to steal by individuals who would use them for substance abuse.

Some hospitals allow one large SHARPS CONTAINER to be left in each hospital room, entirely unsupervised, until it is filled to the top with spent syringes. A child or irresponsible adult might remove some of the syringes out of curiosity. Thus, the risk of an inadvertent needle-stick injury actually increases as these intact syringes are stored in locations that are convenient to the clinical staff prior to disposal.

Another method of disposing of the syringes is to use a SHARPS CONTAINER that has a notched port into which the typical LUER-LOC needle tip can be fitted and unscrewed allowing the needle to fall into the container. The disadvantage to this method is that the process of unscrewing the needle tip almost always requires one hand to hold the container while the other hand rotates the body of the syringe. The clinician risks a needle-stick injury as he/she brings one hand onto the SHARPS CONTAINER while the other hand with the exposed syringe needle is brought down to the same location to insert into the collector. This action may be further complicated by the amount of space available for the activity, the location of the SHARPS CONTAINER, the size of the container, and many other possible factors.

Turning now to patented prior art, a number of inventors have tried to deal with the risks of needle-stick injury and cross-contamination.

U.S. Pat. No. 3,648,695 to Bowen (1972) discloses a pressurized applicator for formed medications which has an ejectable tip. The device cannot be used to aspirate fluids making it possible to load medicines from dispensing vials, to draw blood or bodily fluids, or to aspirate as a precautionary action to determine the anatomical location of the cannula tip relative to venous and arterial structures.

The barrel of the pressurized applicator and its corresponding applicator tip are designed for foam applications and will not provide an adequate seal for fluids having low viscosities. Additionally, the high cost of manufacture severely limits the use of this device for routine delivery of medication.

U.S. Pat. No. 4,026,287 to Haller (1977) shows a method by which the cannula bearing section of the syringe can be separated from the barrel and subsequently retracted within the barrel. The major drawback to this design is that the syringe must be disposed of in large bulk containers as described earlier. There remains the likelihood that after retraction the cannula may be re-exposed by subsequent forward pressure against the plunger rod. It is also possible for the cannula to dislodge from its attachment to the plunger enabling it to fall out of its barrel.

U.S. Pat. No. 3,320,954 to Cowley (1967) shows a method of separating the cannula from the syringe by means of a score located on an adaptor. The syringe is recapped after use and then the cap and syringe barrel are cocked simultaneously causing separation at a score line. U.S. Pat. No. 3,712,302 to Burke et al. (1973) shows a flexible needle guard which can be placed over a contaminated cannula to effect separation of the needle by continuous side to side motion. U.S. Pat. No. 4,027,669 to Johnston et al. (1977) shows a modified LUER-LOK syringe in which after injection the needle is recapped and the cap is cocked in a manner similar to that described by Cowley. All three of the above inventions have the disadvantage of requiring re-capping of the contaminated syringe in order to affect the separation and subsequent disposal of the cannula.

U.S. Pat. No. 4,233,975 to Yerman (1980) shows a design which renders a spent syringe unusable via an internal fluid blocking mechanism. U.S. Pat. Nos. 3,234,944 and Re. 28,713 to Stevens et al. (1962 and 1976) shows a method of supporting the needle on a hypodermic syringe. Neither of these patents relate to safe disposal of the contaminated cannula.

The present invention relates to safe, expeditious, and convenient disposal of the syringe cannula without requiring the operator to risk injury by recapping or otherwise placing bodily parts near the contaminated cannula. All of the existing prior art forms require recapping or dangerous manipulation of the syringe, or do not deal effectively with the safe cannula disposal issues related above.

OBJECTS AND ADVANTAGES

It is therefore a primary object of the present invention to provide a safer method of cannula disposal following routine use of the hypodermic syringe.

It is another object to provide a safe method of cannula removal without the necessity of placing fingers or other bodily parts on or near the contaminated cannula.

Yet another object is to provide a means of cannula removal from the syringe whereby proper disposal of the contaminated cannula can occur immediately after syringe use.

Still another object is to provide separation of the cannula from the syringe so that it may be disposed of in a collector of convenient size.

Another important object is to provide a convenient method of disposal that reduces the possibility of reassembly of the syringe by unauthorized persons.

Yet another object is to provide a method of cannula removal that is easily accomplished with minimal manipulation of the syringe.

Still another object is to provide devices which resemble in form and function the existing available hypodermic syringes.

Another object is to provide devices which are easy to manufacture based on existing materials and technology.

Further objects and advantages will become apparent based on consideration of the ensuing description and drawings.

BRIEF DESCRIPTION OF THE DRAWINGS

FIG. 1 is a perspective view of the preferred embodiment.

FIG. 2 is a partial axial cross-sectional view in elevation of the device of FIG. 1 shown in a more closed position and drawn to a larger scale.

FIG. 3 is an exploded axial cross-sectional side view in elevation of the device of FIG. 1.

FIG. 4 is an enlarged end view in elevation taken in the direction of Arrow 31 of the barrel shown in FIG. 3.

FIG. 5 is an enlarged end view in elevation taken in the direction of Arrow 47 of the plunger rod of FIG. 3.

FIG. 6 is an enlarged end view in elevation taken in the direction of Arrow 71 of the plunger rod of FIG. 3.

FIG. 7 is an exploded axial, partly in section, cross sectional side view in elevation of a second embodiment.

FIG. 8 is a plan view in elevation of the assembled embodiment of FIG. 7.

FIG. 9 is a partial sectional view in elevation of the plunger rod with a modified rubber stopper.

FIG. 10 is an enlarged cross-section taken substantially at 10—10 of FIG. 8.

FIG. 11 is an enlarged cross-section taken substantially at 11—11 of FIG. 9.

FIG. 12 is a partial axial cross-sectional view in elevation of the device of FIG. 7 after function.

FIG. 13 is an exploded axial, partly in section, cross-sectional side view in elevation of a third embodiment.

FIG. 14 is an end view in elevation taken in the direction of Arrow 265 of the plunger rod of FIG. 13.

FIG. 15 is an end view in elevation taken in the direction of Arrow 231 of the needle hub of FIG. 13.

DETAILED DESCRIPTION

Referring now in detail to the drawings wherein like characters refer to like elements throughout the various views, there is generally shown in FIG. 1 an overview 20 of a syringe of the preferred embodiment having a barrel 22 into which a plunger rod 23 and a resilient stopper 26 attached thereto are slideably inserted into an open barrel end 28. Onto the front of the barrel 22 is attached a needle hub 30 which has a cannula 32 therein attached.

FIG. 3 shows the components of the invention prior to assembly. It can be seen that the barrel 22 has a partially closed front end and a front barrel orifice 34 which gently converges as it approaches a barrel lumen 36. The rear end of the barrel 22 is an open end 28 while the material surrounding the open end 28 diverges to form a planar ovoid finger grasp 29. Projecting from the front of the barrel 22 is a barrel lip surface 38.

The needle hub 30 contains a cannula fastening device 40 to permanently affix the cannula 32. In its frontmost aspect the hub converges to form a post 42 onto which a needle cover 44 can be fitted. Diverging toward the rear aspect of the needle hub 30 is an annular rib 46 which is circumscribed about the hub 30. A recess 48 created within the walls of the annular rib 46, is coincident with the shape of the barrel lip surface 38. Projecting rearward from the needle hub 30 and continuous with it, is a hollow generally cylindrical member 50. The member 50 has within it a concavity 52 which is continuous with the lumen of the cannula 32. The most distal aspect of member 50 forms a flare 54 which coincides with the shape of a front fluid wall 56 of the barrel 22. The hub 30 and the barrel 22 may be manufactured of POLYPROPYLENE or other suitable materials to allow deformation of the hub 30 and barrel 22 such that the hub 30 can be snapped onto the front of the barrel 22.

FIG. 4 is an end view taken in the direction of Arrow 31, of the front end of the barrel 22 which includes the front barrel orifice 34 and the surrounding lip surface 38 including a back end view of finger grasp 29. FIG. 5 is an end view of the needle hub 30 with its various components taken in the direction of Arrow 47.

The plunger rod 23 as shown in FIG. 3 has at its most rearward aspect a disk shaped planar surface to serve as a thumbrest 60. The plunger rod 23 is generally of cruciform shape in cross-section and of suitable length to slide the mounted resilient stopper 26 into contact with the front fluid wall 56 of the barrel 22. Toward the front aspect of the plunger rod 23 the cruciform shape merges with a planar stopper backing 62. Emerging from and continuous with the stopper backing 62 is a cruciform shaped extension 64 of a size smaller in cross-section than the general portion of the plunger rod 23. Emerging from and continuous with the extension 64 is a disk shaped stopper stabilizer 66. The stabilizer 66 may be located a few millimeters forward of the stopper backing 62 and has a taper 68 on its outer circumference that converges toward the front of the plunger rod 23 thereby allowing the resilient stopper 26 to be snapped onto the front of the plunger rod 23 with ease. Further forward of extension 64 is a forward tapering plunger tip 70 into which the extension 64 merges. The plunger tip 70 has a tip groove 71 circumscribed about it for the purpose of stabilizing the front aspect of the resilient stopper 26. FIG. 6 is an end view taken in the direction of Arrow 71 of the front end of the plunger rod 23.

The resilient stopper 26 as seen in cross-section in FIG. 3 has a flat rear surface and has circumscribed about it two annular fluid seals 72. The stopper 26 is generally hollow in the unassembled form with an open rear stopper end 74. Within the lumen of the stopper 26 is a retention groove 76 corresponding to the general shape of the stopper stabilizer 66. The lumen of stopper 26 widens considerably toward the front aspect of the stopper 26 to form a collapsing space 78. It then subsequently tapers to form a plunger tip orifice 80.

As shown in FIG. 2 when the components are assembled the stopper 26 lies within the barrel 22. The front aspect of the plunger rod 23 lies within the lumen of the stopper 26 while the greater part of the plunger rod 23 may be located to some degree within the barrel 22. The rear aspect of the plunger rod 23 protrudes from the open barrel end 28. The needle hub 30 with its needle cover 44 are snapped onto the front of the barrel. Thus, the plunger rod 23 with the attached resilient stopper 26 provide a fluid-sealing engagement with the internal surface of the barrel so that fluids or medications can be aspirated and injected through the cannula 32. All parts of the preferred embodiment can be assembled by utilizing compressive forces.

FIG. 7 is an exploded view partially in section of a second embodiment of the invention. In this embodiment a needle hub 130 with its mounted cannula 132 may be constructed as a part of a barrel 122. Continuous with the inner surface of the hub 130 is a compression contour 148 which is molded as an integral part within the hub 130 and is circumscribed therein. Lying adjacent to the contour 148 on the outer aspect of the hub 130 and circumscribed thereabout is a score 146 of sufficient depth so as to create a frangible means of separation of the front of the syringe. The barrel 122 has at its rearward end a planar finger grasp 129 surrounding the open end 128.

A plunger rod 123 is shown having a planar surface at its rearmost aspect which forms a thumbrest 160. The plunger rod 123 is generally of cruciform shape in cross-section as described in the preferred embodiment. The plunger rod 123 includes a planar stopper backing 162. Emerging from the stopper backing 162 is an extension 164 also of cruciform shape in cross-section which tapers to a constant width forward of the stopper backing 162. Arising from and continuous with the extension 164 is an elongated cone shaped piston 170 having a wide flat base 171 at its rearmost aspect and a gently rounded apex 173 at its frontmost aspect.

A resilient stopper 126 is provided with two annular fluid seals 172. The stopper 126 is generally hollow with an internal contour corresponding to the taper of the extension 164. The stopper 126 is inserted over the piston 170 and extension 164 such that it lies between the stopper backing 162 and the base of the piston 170. The plunger rod 123 with its mounted resilient stopper 126 comprises a plunger 124 which is seen in FIG. 8.

FIG. 8 shows the second embodiment in its assembled form. An optional feature of the second embodiment is a series of narrow tabular elevations 138 which protrude from the internal barrel wall to limit the forward movement of the plunger 124. These elevations 138 are also seen in FIG. 10 which is a cross-section of FIG. 8 taken at 10—10 of FIG. 8. Another optional feature for the second embodiment is seen in FIG. 9.

FIG. 9 is an elevational view partially in section of the previously described plunger rod 123 with a modified stopper 177 to partially enclose the apex of the piston 170. The piston 170 has a piston groove 171 circumscribed about it for the purpose of stabilizing the modified stopper 177. The stopper has a collapsing space 178 to permit retraction of the front of the stopper 177 from around the piston 170. FIG. 11 is a cross-section of the plunger rod 123 and its mounted stopper 177 taken at 11—11 of FIG. 9.

FIG. 12 shows the relationship of the parts of the second embodiment after normal syringe use where continued forward plunger movement causes a separation at the score 146.

A third embodiment of the invention is shown in FIG. 13 as an exploded view. In this embodiment a barrel 222 has an external male thread 238 at its partially closed front end which corresponds to an internal female thread 248 within a needle hub 230. A series of slots 252 lie within the inner front surface of the hub 230 and are therein continuous with the lumen of a cannula 232. A plunger rod 223 is provided having a round planar surface at its rearmost aspect which serves as a thumbrest 260. The thumbrest 260 may be knurled about its periphery. The plunger rod 223 is generally of cruciform shape in cross-section. The forward aspect of the plunger rod 223 merges with a planar surface which serves as a stopper backing 262. Arising from the front of the stopper backing 262 is an extension 264 also of cruciform shape in cross-section. The extension 264 narrows as it courses forward of the stopper backing 262 and merges with a planar surface which is a forward stopper plate 266. Extending from the front of the forward stopper plate 266 are a series of converging prongs 270. The prongs 270 are capable of engaging the slots 252 of the hub 230. A resilient stopper 226 is provided which is generally hollow, having an internal surface which tapers coincidentally with the extension 264. The stopper 226 is slid over the prongs 270 so that the stopper 226 lies between the stopper backing 262 and the forward stopper plate 266. The plunger rod 223 with its mounted resilient stopper 226 comprise a means of fluid sealing engagement with the syringe barrel 222.

The needle hub 230 is screwed onto the threaded end of the barrel 222. The plunger rod 223 with its mounted resilient stopper 226 are inserted into the open rear end of the barrel 222 to complete assembly.

FIG. 14 shows an end view of the plunger rod 223 taken in the direction of Arrow 265 of FIG. 13 without the resilient stopper 226. FIG. 15 is an end view of the hub 230, taken in the direction of Arrow 231.

OPERATION

Turning now to use of the invention, it can be observed from FIGS. 1 and 2 that the preferred embodiment will function in a similar manner to other syringes. Medications can be aspirated from storage vials through the cannula 32 and the concavity 52 into the lumen of the barrel 22. Injection of the medication can be made in the normal manner with aspiration possible where needed. The needle hub 30 will be stabilized by the annular rib 46 to prevent lateral forces from dislodging it. The hollow member 50 with its end flare 54 provides a mechanical lock and fluid seal that improves as pressure against flare 54 increases. As the greater extent of the medication has been injected the resilient stopper 26 comes to contact the cylindrical member 50.

Additional forward plunger force applied against the thumbrest 60 can be applied. Such force of greater magnitude than that required for the injection is capable of forcing the plunger tip 70 into the concavity 52 while causing simultaneous retraction of the front aspect of the stopper 26 from around the plunger tip 70. This inversion of the front surface of the stopper is aided by the presence of the collapsing space 78. The continuation of the forward plunger motion under thumb pressure will ultimately result in the dislodgement of the needle hub 30 from the syringe 20 as plunger forces become concentrated in a small area coinciding with the longitudinal axis of the needle hub 30. The hub retaining forces provided by the annular rib 46 and the flare 54 are overcome by the increasing forward plunger forces which allow distortion of the flare 54 and annular rib 46 to the extent required for a forward dislodgement of the needle hub 30 from the syringe.

The preferred embodiment possesses a number of significant features. The relationship between the structures of the barrel 22 and the needle hub 30 allows the hub 30 to be snapped onto the front of the barrel 22 while imparting both stability and fluid sealing properties to the hub 30. The oblong shape of the concavity 52 and the corresponding length of the plunger tip 70 imparts a predictable forward ejection of the needle hub 30 without the risk of a lateral or eratic hub ejection. The forward tapering of the plunger tip 70 ensures engagement into the slightly wider and correspondingly tapered concavity 52. The collapsing space 78 of the stopper 26 allows the forward aspect of the stopper 26 to retract thereby exposing the plunger tip 70.

Thus, immediately following injection or other use of the invention, the syringe may be held over a suitable SHARPS CONTAINER and forward plunger force can be exerted resulting in ejection of the contaminated cannula. This accomplishes:

(a) an expeditious one handed disposal of the cannula;
(b) a method of cannula disposal that does not require recapping or other dangerous manipulation of the syringe;
(c) a significant reduction in the volume of hazardous waste since the infectious portion of the syringe, the cannula, can be disposed of in a SHARPS CONTAINER of very small size;
(d) a convenient method of cannula disposal since the necessary SHARPS CONTAINERS can be made with less than a pint of volume and still dispose of a great quantity of infectious cannulas; and
(e) a method of cannula disposal that causes separation of the cannula from the syringe allowing for disposal practices that discourage reassembly by unauthorized individuals.

Referring to FIGS. 7, 8, 9, 10, 11, and 12 it can be seen that the second embodiment functions in a similar manner to the preferred embodiment. The components shown in FIG. 7 are assembled to provide the invention shown in FIG. 8. Aspiration and injection of medications are performed in the usual manner. After the injection has been made the syringe is withdrawn and the contaminated cannula is held over a suitable SHARPS CONTAINER. Continued forward pressure against the thumbrest 160 will cause the piston 170 to move into the lumen of the needle hub 130 such that the tip of the piston 170 lies against the compression contour 148. At this point a force of greater magnitude is employed against the thumbrest 160 which spreads the hub 130 laterally as the piston 170 further engages the compression contour 148.

Referring to FIG. 12 it can be seen that ultimately the deformation of the hub 130 results in its separation as the plastic shears at the score 146. The forward momentum of the plunger 124, the weight of the cannula containing portion of the hub 130 and the elastic properties of the plastic enable the cannula containing portion of the hub 130 to fall free of the syringe into a suitable SHARPS CONTAINER of convenient size.

The elongated shape of the piston 170 serves to reduce the amount of thumb force needed to cause the separation since lateral spreading forces near the score 146 are induced by a significantly long plunger motion. The elongated shape of the piston 170 also imparts forward direction to the separated portion of hub 130 thus preventing an undesired lateral separation.

As shown in FIGS. 8 and 10 an optional series of tabular elevations 138 exist to prompt the operator that the injection has been completed. These elevations 138 will temporarily prevent continued forward motion of the piston 170 toward the compression contour 148. After the completion of the injection an additional force against the thumb rest 160 will cause the stopper 126 to move over the elevations 138 so that still further forces can be applied to affect the cannula separation.

FIG. 9 shows the modified stopper 177 with the collapsing space 178 similar to the stopper 26 described above. The front aspect of stopper 177 will invert as it is forced against the front wall of barrel 122 thereby exposing the piston 170 and enabling piston 170 to function as described above. This second embodiment of the invention possesses all of the same objects and advantages attributed to the preferred embodiment and is operated in the same manner. It differs from the preferred embodiment primarily in structure.

Referring now to FIGS. 13, 14, and 15 it can be seen that assembly of the third embodiment requires that the stopper 226 be placed over the prongs 270 and thus inserted between the forward stopper plate 266 and the stopper backing 262. The needle hub 230 is screwed onto the external male threads 238 of the barrel 222. The plunger which is comprised of the plunger rod 223 and its mounted resilient stopper 226 is inserted into the rearward end of the syringe barrel 222. Aspiration and injection may be made in the usual manner. Following the injection the syringe may be held over a suitable sharps container and the hub slots 252 of the needle hub 230 can be internally engaged by the prongs 270 of the plunger rod 223. The thumb rest 260 may then be rotated to unscrew the needle hub 230 from the barrel 222. Thus, the cannula bearing portion of the syringe may be disposed of into a SHARPS CONTAINER of convenient size without need of placing fingers or other body parts near the contaminated cannula.

SUMMARY AND SCOPE

Accordingly, the reader will see that the invention by its nature represents a significant improvement in the design and usage of the hypodermic syringe. The risk of contracting a serious or lethal disease through an inadvertent needle-stick wound is lessened significantly when a clinician utilizes the invention and disposal methods as described above. Other risks to the public are averted as well since disposal methods are dramatically improved.

Although the above descriptions contain many specificities, these should not be construed as limiting the scope or spirit of the invention. Many variations of the shape and size of the invention are possible as are variations in the shape and size of the above described components and the scope of the invention should be determined by the appended claims and their legal equivalents, rather than by the examples given.

What I claim and wish to protect by Letters Patent is:

1. A hypodermic syringe comprising:
a barrel having a first open end and a second partially open end,
a hypodermic needle cannula having a needle hub fractionally attachable to said second end of said barrel,
a plunger slideable within said barrel and formed with a first and second end,
said second end of said plunger having a plunger tip means extendable through said second end of said barrel and engageable with said needle hub to tonge said needle hub off of said barrel.

2. The device of claim 1 wherein:
said needle hub is attachable to said second end of said barrel by a mating compression fitting.

3. The device of claim 1 further comprising:
a resilient stopper mounted on said plunger tip and formed with a central opering,
said plunger tip having a cone portion extendable through said stopper to engage said needle hub.

4. The device of claim 3 wherein:
said stopper is made of rubber.

5. The device of claim 3 wherein:
said stopper is generally cylindrical having an open end and a closed end joined by an annular sidewall, said open end being mounted on said second end of said plunger, and said sidewall is formed with an exterior surface slideably engageable with said barrel and an interior surface extending substantially parallel to said exterior surface but having a flared portion adjacent the intersection of said sidewall with said closed end to facilitate collapse of said sidewall.

6. The device of claim 5 wherein:
said closed end of said stopper is formed with an aperture to facilitate passage of said plunger tip through said closed end of said stopper to engage said needle hub.

7. The device of claim 1 wherein:
said needle hub is threadedly connected to said second end of said barrel and is formed with a recess adjacent said second end of said barrel, and
said plunger tip is formed to mate with said recess and said plunger is rotatable within said barrel to enable said plunger tip to unthread said needle hub from said barrel.

8. The device of claim 7 wherein:
said recess is cruciform.

9. The device of claim 3 further comprising:
means located within said barrel and engageable by said stopper to provide a tactile indication to the user when said stopper reaches a predetermined position within said barrel.

* * * * *